(12) United States Patent
Mouscadet et al.

(10) Patent No.: US 11,946,107 B2
(45) Date of Patent: Apr. 2, 2024

(54) **METHOD OF DETECTING *SALMONELLA TYPHIMURIUM***

(71) Applicant: Bio-Rad Europe GmbH, Basel (CH)

(72) Inventors: Jean-Francois Mouscadet, Basel (CH); Sophie Pierre, Paris (FR)

(73) Assignee: Bio-Rad Europe GmbH, Basel (CH)

( * ) Notice: Subject to any disclaimer, the term of this patent is extended or adjusted under 35 U.S.C. 154(b) by 533 days.

(21) Appl. No.: 16/310,809

(22) PCT Filed: Jun. 15, 2017

(86) PCT No.: PCT/IB2017/000921
§ 371 (c)(1),
(2) Date: Dec. 17, 2018

(87) PCT Pub. No.: WO2017/216635
PCT Pub. Date: Dec. 21, 2017

(65) Prior Publication Data
US 2019/0177773 A1 Jun. 13, 2019

Related U.S. Application Data

(60) Provisional application No. 62/351,130, filed on Jun. 16, 2016.

(51) Int. Cl.
*C12Q 1/689* (2018.01)
*C12Q 1/686* (2018.01)

(52) U.S. Cl.
CPC ............ *C12Q 1/689* (2013.01); *C12Q 1/686* (2013.01); *C12Q 2600/166* (2013.01); *G01N 2333/255* (2013.01)

(58) Field of Classification Search
None
See application file for complete search history.

(56) References Cited

U.S. PATENT DOCUMENTS

| | | |
|---|---|---|
| 6,258,569 B1 | 7/2001 | Livak et al. |
| 6,814,934 B1 | 11/2004 | Higuchi |
| 7,476,733 B2 | 1/2009 | Carvalho et al. |
| 7,799,522 B2 | 9/2010 | Li et al. |
| 8,268,984 B2 | 9/2012 | Tourniaire |

FOREIGN PATENT DOCUMENTS

| | | |
|---|---|---|
| CN | 101 705 307 A | 5/2010 |
| CN | 102618634 A | 8/2012 |
| CN | 103293297 A | 9/2013 |
| CN | 104 087 654 A | 10/2014 |
| CN | 103266179 B | 10/2014 |
| CN | 104 830 988 A | 8/2015 |
| EP | 1911852 A1 | 7/2009 |
| WO | 95/00664 A1 | 1/1995 |
| WO | 2015026757 A2 | 2/2015 |
| WO | 2015148785 A1 | 10/2015 |

OTHER PUBLICATIONS

Singh (Molecular and Cellular Probes, 2013, 27, 80-85).*
Liu (Food Control 2012, 27, 87-93).*
McClelland et al., "Complete genome sequence of *Salmonella enterica* serovar Typhimurium LT2." Nature. Oct. 23, 2001, vol. 413, pp. 852-856.
Bio-Rad Laboratories, Inc. User Guide for iQ-Check *Salmonella* II Kit. Catalog #: 357-8123. Code 808463. Revision G date: Feb. 2015; pp. 1-20.
ThermoFisher Scientific. User guide for TaqMan Assays for Food and Environmental Testing: Real-time PCR detection of pathogens in food and environmental samples. Publication No. MAN0009391, Revision C date: May 20, 2015; pp. 1-30.
Alvarez, et al. "Development of Multiplex PCR Technique for Detection and Epidemiological Typing of *Salmonella* in Human Clinical Samples." Journal of Clinical Microbiology, Apr. 2004, vol. 42, No. 4, p. 1734-1738.
Beaubrun et al. "The evaluation of a PCR-based method for identification of *Salmonella enterica* serotypes from environmental samples and various food matrices," Food Microbiology, 2012. vol. 31, pp. 199-209.
Hadjinicolaou et al. "Molecular beacon-based real-time PCR detection of primary isolates of *Salmonella typhimurium* and *Salmonella enteritidis* in environmental and clinical samples." BMC Microbiology, May 19, 2009, vol. 9, No. 97, pp. 1-14.
Lee et al. "A multiplex real-time PCR for differential detection and quantification of *Salmonella* ssp., *Salmonella enterica* serovar Typhimurium and Enteritidis in meats," Journal of Veterinary Science, 2009, vol. 10, No. 1, pp. 43-51.
McCarthy et al. "Sensitive and Rapid Molecular Detection Assays for *Salmonella enterica* serovars Typhimurium and heidelberg," Journal of Food Protection, Mar. 25, 2009. vol. 72, No. 11, 2009, pp. 2350-2357.
Park et al. "Identification of *Salmonella enterica* subspecies I, *Salmonella enterica* serovars Typhimurium, Enteritidis and Typhi using multiplex PCR," FEEMS Microbiol lett, May 13, 2009, vol. 301, pp. 137-146.
Pui et al. "Multiplex PCR for the concurrent detection and differentiation of *Salmonella* spp., *Salmonella typhi* and *Salmonella typhimurium*, " Tropical Medicine and Health, 2011. vol. 39, No. 1, pp. 9-15.
Shanmugasundaram et al. "Detection of *Salmonella enterica* serovar Typhimurium by selective amplification of fliC, fliB, iroB, invA, rfbJ, STM2755, STM4497 genes by polymerase chain reaction in a monoplex and multiplex format," World J Microbiol Biotechnol, Mar. 19, 2009, vol. 25, pp. 1385-1394.
Bioneer AccuPower® *Salmonella* Spp. 3-Plex PCR kit, downloaded on Apr. 9, 2019. Url: https://eng.bioneer.com/index.php/20-mas-1115.html.
Biotecon Diagnostics GmbH. User manual for foodproof® *Salmonella enteritidis* and Typhimurium Detection LyoKit-5'Nuclease—Version 2, Mar. 2017, pp. 1-9.
Anicon Labor GmBH directions for use for Kylt® SE/ST Triplex Real-Time PCR Detection Kit for detection of *Salmonella enteritidis* and *Salmonella typhimurium*. Publication No. FS.DNA-DK.SE/ST. 02, Rev001, Dec. 2017. pp. 1-8.
Kim, H.J., et al. "Identification of *Salmonella enterica* serovar Typhimurium using Specific PCR Primers obtained by Comparative Genomics in *Salmonella serovars*," J Food Prot., vol. 69, No. 7, Jul. 1, 2006, pp. 1653-1661.
International Search Report, dated Oct. 2, 2017, for corresponding International Patent Application PCT/IB2017/000921, 5 pages.
Written Opinion, dated Oct. 2, 2017, for corresponding International Patent Application PCT/IB2017/000921, 5 pages.
English translation of Office Action dated Jan. 4, 2022 in CN Patent Application No. 201780037629.5. 17 pages.

* cited by examiner

*Primary Examiner* — Sarae L Bausch
(74) *Attorney, Agent, or Firm* — Kilpatrick Townsend & Stockton LLP

(57) ABSTRACT

Provided herein are methods and compositions for detecting *Salmonella typhimurium* in a sample.

11 Claims, No Drawings
Specification includes a Sequence Listing.

SEQUENCE LISTING

<160> NUMBER OF SEQ ID NOS: 9

<210> SEQ ID NO 1
<211> LENGTH: 1388
<212> TYPE: DNA
<213> ORGANISM: Salmonella typhimurium

<400> SEQUENCE: 1

| | | | | | |
|---|---|---|---|---|---|
| atgtagctta | agatatctat | agtgatatca | gtgtaatact | tattggttag | atcggtatga | 60 |
| tcttgaatat | ttttatatcg | atagtttgga | ttacatagta | gagttatttc | actttgcaat | 120 |
| acagctttaa | ttatagtttt | gtcaagttgt | aatttatcta | taaaaatatt | atttatagta | 180 |
| ttttctatta | ggagaagtgt | ttcgactaac | ttgatatttg | tattgatttt | ttgtttgtag | 240 |
| atattccgta | gcaattgagt | tgaattgtgt | tcaagcaatg | gtgaacaaac | ataatcccat | 300 |
| gattgctctt | gagagtccca | gtcattttta | gctatttcaa | tagcattggt | gactaattcg | 360 |
| ataatttcat | cttcaatttc | tggatatggt | actgaggcta | attcaccact | agtaaagcta | 420 |
| agtgtggggg | ctagtattga | taaataatgg | tttacaaccg | gagtgcacat | taatcccgca | 480 |
| gcgtaaagca | actcattttt | gttatttgaa | aagccgcaac | ggcctgtatc | atcaaaaaca | 540 |
| aacccttttg | gacgatatct | cacgcaaaaa | ttaccttggc | ttattttttga | ccatgttatg | 600 |
| ccttctctaa | agtaatactc | atcatttctt | acggcagagc | gagttttgcc | attctcaaat | 660 |
| ttaaaatttc | gtatttcgta | accattattt | tcccaattta | caactatttc | gttattacca | 720 |
| taccactttc | gatattcacc | tccactacta | caaggaaacc | atttgatatt | atgaatgtcg | 780 |
| attttttgtat | ttgattcttt | atttgtgata | agggttttttt | ttattgaaac | ctcgtaccaa | 840 |
| tatctttgaa | atttaatatt | gtcaccggtg | gacatgcctg | cttttaatgc | tatttttct | 900 |
| ccaagttttt | tatggtggcg | aaaagataat | agactcggta | agtctatcca | atatgctatt | 960 |
| ggcattcctg | gtatgttttt | aaaatcatgc | tgtgtaaatt | tatcaaatat | attttttcctt | 1020 |
| agaagtagat | cgcttttctt | tacttcttcc | ctaccatcta | aagtctaaa | aaatacaggt | 1080 |
| tggtaacgtt | cggagtgttg | gttttttaatc | acccaggcag | ttgtctgtac | aacctctcca | 1140 |
| gaaatttgcc | caaaagcccg | agctcccaaa | tgtgccatcg | taataaatgt | tttattgtcc | 1200 |
| aataaccagt | tacgtagtgc | ttcataactt | gacaaaaaca | tccatgattg | catattgact | 1260 |
| tgagcattaa | acccatttcc | tttaagcaaa | gaaaatgcat | tctgcataaa | cattgcaaac | 1320 |
| aaatcagctt | tactatccgg | gaagttattt | ttggcaaact | ctttcagctc | actattcatt | 1380 |
| cccttgcc | | | | | 1388 |

<210> SEQ ID NO 2
<211> LENGTH: 947
<212> TYPE: DNA
<213> ORGANISM: Salmonella typhimurium

<400> SEQUENCE: 2

| | | | | | |
|---|---|---|---|---|---|
| atgtagctta | agatatctat | agtgatatca | gtgtaatact | tattggttag | atcggtatga | 60 |
| tcttgaatat | ttttatatcg | atagtttgga | ttacatagta | gagttatttc | actttgcaat | 120 |
| acagctttaa | ttatagtttt | gtcaagttgt | aatttatcta | taaaaatatt | atttatagta | 180 |
| ttttctatta | ggagaagtgt | ttcgactaac | ttgatatttg | tattgatttt | ttgtttgtag | 240 |
| atattccgta | gcaattgagt | tgaattgtgt | tcaagcaatg | gtgaacaaac | ataatcccat | 300 |
| gattgctctt | gagagtccca | gtcattttta | gctatttcaa | tagcattggt | gactaattcg | 360 |
| ataatttcat | cttcaatttc | tggatatggt | actgaggcta | attcaccact | agtaaagcta | 420 |

```
agtgtggggg ctagtattga taaataatgg tttacaaccg gagtgcacat taatcccgca      480
gcgtaaagca actcattttt gttatttgaa aagccgcaac ggcctgtatc atcaaaaaca      540
aacccttttg gacgatatct cacgcaaaaa ttaccttggc ttattttga ccatgttatg       600 ccttctctaa agtaatactc atcatttctt acggcagagc gagttttgcc attctcaaat      660
ttaaaatttc gtatttcgta accattattt tcccaattta caactatttc gttattacca     720
taccactttc gatattcacc tccactacta caaggaaacc atttgatatt atgaatgtcg      780 attttttgtat ttgattcttt atttgtgata agggtttttt ttattgaaac ctcgtaccaa    840
tatctttgaa atttaatatt gtcaccggtg gacatgcctg cttttaatgc tattttttct     900
ccaagttttt tatggtggcg aaaagataat agactcggta agtctat                   947
```

```
<210> SEQ ID NO 3
<211> LENGTH: 123
<212> TYPE: DNA
<213> ORGANISM: Salmonella typhimurium

<400> SEQUENCE: 3
taggagaagt gtttcgacta acttgatatt tgtattgatt ttttgtttgt agatattccg      60
tagcaattga gttgaattgt gttcaagcaa tggtgaacaa acataatccc atgattgctc     120
ttg                                                                  123

<210> SEQ ID NO 4
<211> LENGTH: 22
<212> TYPE: DNA
<213> ORGANISM: Artificial Sequence
<220> FEATURE:
<223> OTHER INFORMATION: synthetic forward primer

<400> SEQUENCE: 4
taggagaagt gtttcgacta ac                                              22

<210> SEQ ID NO 5
<211> LENGTH: 22
<212> TYPE: DNA
<213> ORGANISM: Artificial Sequence
<220> FEATURE:
<223> OTHER INFORMATION: synthetic reverse primer

<400> SEQUENCE: 5
caagagcaat catgggatta tg                                              22

<210> SEQ ID NO 6
<211> LENGTH: 29
<212> TYPE: DNA
<213> ORGANISM: Artificial Sequence
<220> FEATURE:
<223> OTHER INFORMATION: synthetic probe

<400> SEQUENCE: 6
tttacaattg agttgaattg tgttcaagc                                       29

<210> SEQ ID NO 7
<211> LENGTH: 30
<212> TYPE: DNA
<213> ORGANISM: Artificial Sequenc
<220> FEATURE:
<223> OTHER INFORMATION: synthetic probe

<400> SEQUENCE: 7
aaaagaacac aattcaactc aattgctacg                                      30
```

```
<210> SEQ ID NO 8
<211> LENGTH: 25
<212> TYPE: DNA
<213> ORGANISM: Artificial Sequence
<220> FEATURE:
<223> OTHER INFORMATION: synthetic probe

<400> SEQUENCE: 8
caattgagtt gaattgtgtt caagc                                           25

<210> SEQ ID NO 9
<211> LENGTH: 26
<212> TYPE: DNA
<213> ORGANISM: Artificial Sequence
<220> FEATURE:
<223> OTHER INFORMATION: synthetic probe

<400> SEQUENCE: 9
gaacacaatt caactcaatt gctacg                                          26
```

METHOD OF DETECTING *SALMONELLA TYPHIMURIUM*

CROSS-REFERENCE TO RELATED APPLICATION

This application is a national phase application under 35 U.S.C. 371 claiming priority to PCT/IB2017/000921, filed Jun. 15, 2017, which claims the benefit of U.S. Application 62/351,130 filed on Jun. 16, 2016, the content of each of which is hereby incorporated by reference in its entirety for all purposes.

SEQUENCE LISTING

The instant application contains a Sequence Listing which has been submitted electronically herewith and is hereby incorporated by reference in its entirety. The ASCII copy, created on Dec. 17, 2018, is named 1050901_SEQ_ST25.txt, and is 5,089 bytes in size.

BACKGROUND

*Salmonella* is a leading cause of foodborne illnesses worldwide, with poultry and pork products being a primary source of infection to humans. Detecting *Salmonella* can be challenging because low levels of the bacteria may not be recovered using traditional culturing techniques. The genus *Salmonella*, member of the Enterobacteriaceae family, comprises two species *Salmonella enterica* and *Salmonella bongori*. *Salmonella enterica* is further divided into six subspecies, of which *S. enterica* subsp. *enterica* is the most clinically significant, causing 99% of *Salmonella* infections. The subspecies are further sub-divided into more than 2,500 serovars defined by somatic and flagellar antigens. *Salmonella enterica* subsp. *enterica* serovar *Typhimurium* and *Salmonella enterica* subsp. *enterica* serovar *Enteritidis* are the most frequently reported serovars associated with human cases of *Salmonella* infection from foodborne outbreaks. In the EU, a regulation in force since 2003 governs the mandatory detection of *Salmonella*. In 2011, this regulation was supplemented with the mandatory testing for *S. enteritidis* and *S. typhimurium*. According to Commission Regulation (EU) No. 1086/2011, all fresh poultry must be examined for *S. enteritidis* and *S. typhimurium* contamination. In the United States, the Food and Drug Administration (FDA) has published the Final Rule "Prevention of *Salmonella enteritidis* in Shell Eggs During Production, Storage, and Transportation" (74 FR 33030), which will introduce methods requiring egg producers to test for *S. enteritidis*. For non-egg producers, the FDA also published the guidance document for testing of human foods for *salmonella*: "Guidance for Industry: Testing for *Salmonella* Species in Human Foods and Direct-Human-Contact Animal Foods".

Conventional microbiological methods for the detection and identification of *Salmonella* serovars are very time consuming. The current accepted method for isolation of *Salmonella* from food and environmental primary production samples takes up to 5 days according to the ISO 6579. The most widely-used method used to characterize *Salmonella* into its subspecies is the Kauffman-White serotyping system, based on the variability of the O, H and Vi antigens.

SUMMARY

Described herein are methods and compositions for detecting *Salmonella typhimurium*.

In an embodiment, a method of selectively detecting the presence of *Salmonella typhimurium* in a sample comprises (a) providing a reaction mixture comprising a suitable primer pair for amplification of residues 749 to 2136 (1388 bp), or a portion thereof, of *Salmonella typhimurium* ACCESSION CP007235 (SEQ ID NO:1); (b) performing PCR amplification of the nucleic acids of the sample using the reaction mixture of step (a); and (c) selectively detecting the presence of *Salmonella typhimurium* by detecting the amplified nucleic acids. In some embodiments, the step (b) is performed in partitions. In some embodiments, the detecting the presence of *Salmonella typhimurium* comprises sequencing the amplified nucleic acids.

In some embodiments, the reaction mixture comprises a primer pair for amplification of a sequence 95%, 97% or 99% homologous to SEQ ID NO:1 or a portion thereof. In certain embodiments, the reaction mixture comprises a primer pair for amplification of residues 749 to 1697 (947 bp), or portions thereof, of *Salmonella typhimurium* ACCESSION CP007235 (SEQ ID NO:2). In some embodiments, the reaction mixture comprises a primer pair for amplification of a sequence 95%, 97% or 99% homologous to SEQ ID NO:2 or a portion thereof. In certain embodiments, the reaction mixture comprises a primer pair for amplification of residues 755 to 1063 (309 bp), or portions thereof, of *Salmonella typhimurium* ACCESSION CP007235 (SEQ ID NO:3). In some embodiments, the reaction mixture comprises a primer pair for amplification of a sequence 95%, 97% or 99% homologous to SEQ ID NO:3 or a portion thereof.

In an embodiment, the primer pair for amplification of the nucleic acid region of SEQ ID NO:3 comprises the polynucleotide sequences set forth in SEQ ID NO:4 and SEQ ID NO:5. In an embodiment, the reaction mixture further comprises a probe for the nucleic acid region to be detected. In some embodiments, the probe comprises a detectable label. In some embodiment, the probe comprises the polynucleotide sequences set forth in SEQ ID NO:6 and SEQ ID NO:7. In certain embodiments, the probe comprises the polynucleotide sequences set forth in SEQ ID NO:6, SEQ ID NO:7, SEQ ID NO:8, or SEQ ID NO:9.

In an embodiment, an isolated polynucleotide comprises a polynucleotide sequence having at least 95% sequence identity based on the BLASTN method of alignment to the polynucleotide sequence set forth in SEQ ID NO:1. In some embodiments, the isolated polynucleotide sequence comprises a polynucleotide sequence set forth in SEQ ID NO:1. In an embodiment, an isolated polynucleotide comprises a polynucleotide sequence having at least 95% sequence identity based on the BLASTN method of alignment to the polynucleotide sequence set forth in SEQ ID NO:2. In some embodiments, the isolated polynucleotide sequence comprises a polynucleotide sequence set forth in SEQ ID NO:2. In an embodiment, an isolated polynucleotide comprises a polynucleotide sequence having at least 95% sequence identity based on the BLASTN method of alignment to the polynucleotide sequence set forth in SEQ ID NO:3. In some embodiments, the isolated polynucleotide sequence comprises a polynucleotide sequence set forth in SEQ ID NO:3.

In an embodiment, a kit for the detection of *Salmonella typhimurium* in a sample comprises a primer pair comprising SEQ ID NO:4 and SEQ ID NO:5. In some embodiments, the kit further comprises a probe comprising SEQ ID NO:6 and SEQ ID NO:7. In some embodiments, the kit further comprises a probe comprising SEQ ID NO:6, SEQ ID NO:7, SEQ ID NO:8, or SEQ ID NO:9. In certain embodiments, the kit further comprises at least one component selected from a lysis reagent, a DNA polymerase, at least one dNTP, a buffer, a negative control, a positive control, and instructions for performing a method to detect the presence of *Salmonella typhimurium* in a nucleic acid sample.

DETAILED DESCRIPTION

Provided herein are methods of selectively detecting the presence of *Salmonella typhimurium* in a sample. Also provided are compositions for use in the detection of *Salmonella typhimurium* in a sample by nucleic acid amplification, e.g., by real-time PCR.

The disclosed detection method finds utility in the detection of *S. typhimurium* in any type of sample, for example in samples for food testing, environmental testing, or human/animal diagnostic testing. Exemplary food samples include, but are not limited to, meats products, poultry (e.g., chicken, turkey), eggs, fish (e.g, cod), cookie dough, produce (e.g, lettuce, tomatoes), dairy (e.g, cheese, milk), milk powder (e.g., infant formula), chocolate (e.g., milk), cocoa, nacho cheese seasoning, pasta, pet food, peanut butter, soy flour, spices, and ready-to-eat food. Environmental samples include, but are not limited to, plastic, sealed concrete, and stainless steel. Other types of samples include, but are not limited to, water, stool, blood, urine, and tissue. Another type of sample includes weeds. The methods may be performed at the farm or processing facility prior to initial packaging, after packaging (e.g., prior to or after export from one country to another), or at the point of sale.

I. DEFINITIONS

Unless defined otherwise, technical and scientific terms used herein have the same meaning as commonly understood by a person of ordinary skill in the art. See, e.g., Lackie, Dictionary of Cell and Molecular Biology, Elsevier ($4^{th}$ ed. 2007); Green et al., Molecular Cloning, a Laboratory Manual (Fourth Edition), Cold Spring Harbor Laboratory Press (Cold Spring Harbor, NY 2012).

The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "nucleic acid" refers to polymers of deoxyribonucleotides or ribonucleotides in either single- or double-stranded form, and complements thereof. The term "polynucleotide" refers to a linear sequence of nucleotides. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides can be purified from a host cell in which they naturally occur. Conventional nucleic acid purification methods known to skilled artisans can be used to obtain isolated polynucleotides. The term also embraces recombinant polynucleotides and chemically synthesized polynucleotides.

The terms "polynucleotide", "polynucleotide sequence", "nucleic acid sequence", and "nucleic acid fragment" are used interchangeably herein. These terms encompass nucleotide sequences and the like. A polynucleotide can be a polymer of RNA or DNA that is single- or double-stranded, that optionally contains synthetic, non-natural, or altered nucleotide bases. A polynucleotide in the form of a polymer of DNA can be comprised of one or more strands of cDNA, genomic DNA, synthetic DNA, or mixtures thereof.

The term "amplification product" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition can comprise the components for nucleic acid replication, for example: nucleotide triphosphates, two (or more) primers with appropriate sequences, thermostable polymerase, buffers, solutes, and proteins.

The term "primer" refers to a synthetic oligonucleotide that is capable of acting as a point of initiation of nucleic acid synthesis or replication along a complementary strand when placed under conditions in which synthesis of a complementary strand is catalyzed by a polymerase. A primer can further contain a detectable label, for example a 5' end label.

The term "probe" refers to a synthetic oligonucleotide that is complementary (though not necessarily fully complementary) to a polynucleotide of interest and forms a duplexed structure by hybridization with at least one strand of the polynucleotide of interest. A probe can further contain a detectable label.

As used herein, the terms "label", "detectable label", and such refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, and ligands (e.g., biotin, avidin, streptavidin, or haptens). A detectable label can also include a combination of a reporter and a quencher.

The term "reporter" refers to a substance or a portion thereof which is capable of exhibiting a detectable signal, which signal can be suppressed by a quencher. The detectable signal of the reporter is, e.g., fluorescence in the detectable range; thus, a reporter can also be a label.

The term "quencher" refers to a substance which is capable of suppressing, reducing, inhibiting, etc., the detectable signal produced by the reporter.

As used herein, the term "quenching" refers to a process whereby, when a reporter and a quencher are in close proximity, and the reporter is excited by an energy source, a substantial portion of the energy of the excited state non-radiatively transfers to the quencher where it either dissipates nonradiatively or is emitted at a different emission wavelength than that of the reporter (e.g., by fluorescence resonance energy transfer or FRET).

The reporter can be selected from fluorescent organic dyes modified with a suitable linking group for attachment to the oligonucleotide, such as to the terminal 3' carbon or terminal 5' carbon. The quencher can also be selected from organic dyes, which may or may not be fluorescent, depending on the embodiment of the invention. Generally, whether the quencher is fluorescent or simply releases the transferred energy from the reporter by non-radiative decay, the absorption band of the quencher should at least substantially overlap the fluorescent emission band of the reporter to optimize the quenching.

Non-fluorescent quenchers or dark quenchers typically function by absorbing energy from excited reporters, but do not release the energy radiatively.

Selection of appropriate reporter-quencher pairs for particular probes can be undertaken in accordance with known techniques. Fluorescent and dark quenchers and their relevant optical properties from which exemplary reporter-quencher pairs can be selected are listed and described, for example, in R. W. Sabnis, HANDBOOK OF FLUORESCENT DYES AND PROBES, John Wiley and Sons, New Jersey, 2015, the content of which is incorporated herein by reference.

Reporter-quencher pairs can be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like.

Suitable examples of quenchers can be selected from 6-carboxy-tetramethyl-rhodamine, 4-(4-dimethylaminophenylazo) benzoic acid (DABCYL), tetramethylrhodamine (TAMRA), BHQ-O™, BHQ-1™, BHQ-2™, and BHQ-3™, each of which are available from Biosearch Technologies, Inc. of Novato, Calif., Qy7™ QSY-9™, QSY-21 TM and QSY-35™, each of which are available from Molecular Probes, Inc, Iowa Black™ FQ available from Integrated DNA Technologies.

Suitable examples of reporters can be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from Applied Biosystems, Cal Fluor dye products (such as, e.g., Cal Fluor Gold 540, Orange 560, Red 590, Red 610, Red 635) available from Biosearch Technologies, Quasar dye products (such as, e.g., Quasar 570, 670, 705) available from Biosearch Technologies, and the like.

The term "percent identity," in the context of two or more nucleic acids, refers to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising a sequence that is at least about 25 nucleotides in length, or over a region that is 50-100 nucleotides in length, or over the entire length of the reference sequence.

The terms "selectively" or "selective" with respect to nucleic acids refers to the discrimination between the target nucleic acid sequence (e.g., target sequence of *Salmonella typhimurium*) over the non-target nucleic acid sequences (e.g., non-target sequence *Salmonella typhimurium*). An assay is selective for a sequence if little or no hybridization of the primer or probe occurs with non-target sequence.

The terms "partitioning" or "partitioned" refer to separating an aqueous solution having one or more of a sample and reactant into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

II. NUCLEIC ACIDS

Genome Detection Regions

A detection method is provided herein that is based on the identification of residues 749 to 2136 (1388 bp) of *Salmonella typhimurium* ACCESSION CP007235 (see SEQ ID NO: 1 in Table 1).

TABLE 1

Sequences

| SEQ ID NO | DESCRIPTION | SEQUENCE |
|---|---|---|
| 1 | 1388 bp fragment from the 3315 bp gene of *Salmonella* Typhimurium ACCESSION CP007235 | ATGTAGCTTAAGATATCTATAGTGATATCAGTGTAATACTTATTGGTTAG<br>ATCGGTATGATCTTGAATATTTTTATATCGATAGTTTGGATTACATAGTA<br>GAGTTATTTCACTTTGCAATACAGCTTTAATTATAGTTTTGTCAAGTTGT<br>AATTTATCTATAAAAATATTATTTATAGTATTTTCTATTAGGAGAAGTGT<br>TTCGACTAACTTGATATTTGTATTGATTTTTTGTTTGTAGATATTCCGTA<br>GCAATTGAGTTGAATTGTGTTCAAGCAATGGTGAACAAACATAATCCCAT<br>GATTGCTCTTGAGAGTCCCAGTCATTTTTAGCTATTTCAATAGCATTGGT<br>GACTAATTCGATAATTTCATCTTCAATTTCTGGATATGGTACTGAGGCTA<br>ATTCACCACTAGTAAAGCTAAGTGTGGGGGCTAGTATTGATAAATAATGG |

TABLE 1-continued

Sequences

| SEQ ID NO | DESCRIPTION | SEQUENCE |
|---|---|---|
| | | TTTACAACCGGAGTGCACATTAATCCCGCAGCGTAAAGCAACTCATTTTT<br>GTTATTTGAAAAGCCGCAACGGCCTGTATCATCAAAAACAAACCCTTTTG<br>GACGATATCTCACGCAAAAATTACCTTGGCTTATTTTTGACCATGTTATG<br>CCTTCTCTAAAGTAATACTCATCATTTCTTACGGCAGAGCGAGTTTTGCC<br>ATTCTCAAATTTAAAATTTCGTATTTCGTAACCATTATTTTCCCAATTTA<br>CAACTATTTCGTTATTACCATACCACTTTCGATATTCACCTCCACTACTA<br>CAAGGAAACCATTTGATATTATGAATGTCGATTTTTGTATTTGATTCTTT<br>ATTTGTGATAAGGGTTTTTTTTATTGAAACCTCGTACCAATATCTTTGAA<br>ATTTAATATTGTCACCGGTGGACATGCCTGCTTTTAATGCTATTTTTTCT<br>CCAAGTTTTTTATGGTGGCGAAAAGATAATAGACTCGGTAAGTCTATCCA<br>ATATGCTATTGGCATTCCTGGTATGTTTTTAAAATCATGCTGTGTAAATT<br>TATCAAATATATTTTTCCTTAGAAGTAGATCGCTTTTCTTTACTTCTTCC<br>CTACCATCTATAAGTCTAAAAAATACAGGTTGGTAACGTTCGGAGTGTTG<br>GTTTTTAATCACCCAGGCAGTTGTCTGTACAACCTCTCCAGAAATTTGCC<br>CAAAAGCCCGAGCTCCCAAATGTGCCATCGTAATAAATGTTTTATTGTCC<br>AATAACCAGTTACGTAGTGCTTCATAACTTGACAAAAACATCCATGATTG<br>CATATTGACTTGAGCATTAAACCCATTTTCTTTAAGCAAAGAAAATGCAT<br>TCTGCATAAACATTGCAAACAAATCAGCTTTACTATCCGGGAAGTTATTT<br>TTGGCAAACTCTTTCAGCTCACTATTCATTCCCTTGCC |
| 2 | 947 bp fragment of *Salmonella* Typhimurium ACCESSION CP007235 | ATGTAGCTTAAGATATCTATAGTGATATCAGTGTAATACTTATTGGTTAG<br>ATCGGTATGATCTTGAATATTTTTATATCGATAGTTTGGATTACATAGTA<br>GAGTTATTTCACTTTGCAATACAGCTTTAATTATAGTTTTGTCAAGTTGT<br>AATTTATCTATAAAAATATTATTTATAGTATTTTCTATTAGGAGAAGTGT<br>TTCGACTAACTTGATATTTGTATTGATTTTTTGTTTGTAGATATTCCGTA<br>GCAATTGAGTTGAATTGTGTTCAAGCAATGGTGAACAAACATAATCCCAT<br>GATTGCTCTTGAGAGTCCCAGTCATTTTTAGCTATTTCAATAGCATTGGT<br>GACTAATTCGATAATTTCATCTTCAATTTCTGGATATGGTACTGAGGCTA<br>ATTCACCACTAGTAAAGCTAAGTGTGGGGGCTAGTATTGATAAATAATGG<br>TTTACAACCGGAGTGCACATTAATCCCGCAGCGTAAAGCAACTCATTTTT<br>GTTATTTGAAAAGCCGCAACGGCCTGTATCATCAAAAACAAACCCTTTTG<br>GACGATATCTCACGCAAAAATTACCTTGGCTTATTTTTGACCATGTTATG<br>CCTTCTCTAAAGTAATACTCATCATTTCTTACGGCAGAGCGAGTTTTGCC<br>ATTCTCAAATTTAAAATTTCGTATTTCGTAACCATTATTTTCCCAATTTA<br>CAACTATTTCGTTATTACCATACCACTTTCGATATTCACCTCCACTACTA<br>CAAGGAAACCATTTGATATTATGAATGTCGATTTTTGTATTTGATTCTTT<br>ATTTGTGATAAGGGTTTTTTTTATTGAAACCTCGTACCAATATCTTTGAA<br>ATTTAATATTGTCACCGGTGGACATGCCTGCTTTTAATGCTATTTTTTCT<br>CCAAGTTTTTTATGGTGGCGAAAAGATAATAGACTCGGTAAGTCTAT |
| 3 | 123 bp fragment of *Salmonella* Typhimurium ACCESSION CP007235 | TAGGAGAAGTGTTTCGACTAACTTGATATTTGTATTGATTTTTTGTTTGT<br>AGATATTCCGTAGCAATTGAGTTGAATTGTGTTCAAGCAATGGTGAACAA<br>ACATAATCCCATGATTGCTCTTG |
| 4 | Forward Primer for 123 bp target sequence spanning residues 937 to 958 | TAGGAGAAGTGTTTCGACTAAC |
| 5 | Reverse Primer for 123 bp target sequence spanning residues 1038 to 1059 | CAAGAGCAATCATGGGATTATG |
| 6 | Probe for 123 bp target sequence spanning residues 1000 to 1024 (5'FAM-3'BkFQ) | TTTACAATTGAGTTGAATTGTGTTCAAGC |
| 7 | Probe for 123 bp target sequence spanning residues 995 to 1020 (5'FAM-3'BkFQ) | AAAAGAACACAATTCAACTCAATTGCTACG |

TABLE 1-continued

| Sequences | | |
|---|---|---|
| SEQ ID NO | DESCRIPTION | SEQUENCE |
| 8 | Probe for 123 bp target sequence spanning residues 1000 to 1024 (5'FAM-3'BkFQ) | CAATTGAGTTGAATTGTGTTCAAGC |
| 9 | Probe for 123 bp target sequence spanning residues 995 to 1020 | GAACACAATTCAACTCAATTGCTACG |

Based on a publicly available software (e.g., BLAST), SEQ ID NO:1 is conserved (e.g., 100% sequence identity) in 672 *Salmonella typhimurium* strains listed by Genbank accession number in Table 2.

TABLE 2

| Strains of *Salmonella Typhimurium* in which SEQ ID NO: 1 is 100% Conserved | | | |
|---|---|---|---|
| LVHC01000004.1 | LAPF01000001.1 | CTPI01000002.1 | CTHF01000003.1 |
| LVHA01000006.1 | LAPD01000063.1 | CTPH01000002.1 | CTHE01000002.1 |
| LVGZ01000004.1 | LAPC01000018.1 | CTPG01000002.1 | CTHD01000002.1 |
| LVGY01000004.1 | LAOX01000013.1 | CTPF01000002.1 | CTHC01000003.1 |
| LVGX01000005.1 | JZAH01000029.1 | CTPE01000003.1 | CTHB01000001.1 |
| LVGW01000004.1 | JZAB01000025.1 | CTPD01000001.1 | CTHA01000002.1 |
| LVGU01000047.1 | JYZR01000005.1 | CTPC01000003.1 | CTGZ01000002.1 |
| LVGT01000051.1 | JYZC01000010.1 | CTPB01000003.1 | CTGY01000002.1 |
| LVGS01000046.1 | JYZB01000030.1 | CTPA01000004.1 | CTGX01000005.1 |
| LVGR01000047.1 | JYYZ01000004.1 | CTOZ01000002.1 | CTGW01000025.1 |
| LVGQ01000013.1 | JYYU01000025.1 | CTOY01000002.1 | CTGV01000002.1 |
| LVGP01000004.1 | JYYT01000016.1 | CTOX01000003.1 | CTGU01000006.1 |
| LVGN01000006.1 | JYYQ01000066.1 | CTOW01000001.1 | CTGT01000002.1 |
| LVGM01000008.1 | JYYL01000011.1 | CTOV01000003.1 | CTGS01000002.1 |
| LVGL01000007.1 | JYYK01000018.1 | CTOU01000002.1 | CTGR01000004.1 |
| LVGK01000003.1 | JYYH01000035.1 | CTOT01000003.1 | CTGQ01000002.1 |
| LVGJ01000009.1 | JYYC01000006.1 | CTOS01000002.1 | CTGP01000004.1 |
| LVGI01000006.1 | JYYB01000003.1 | CTOR01000003.1 | CTGO01000001.1 |
| LVGH01000005.1 | JYYA01000024.1 | CTOQ01000004.1 | CTGN01000001.1 |
| LVGG01000006.1 | JYXZ01000019.1 | CTOP01000003.1 | CTGM01000002.1 |
| LVGF01000006.1 | JYXX01000004.1 | CTOO01000002.1 | CTGL01000004.2 |
| LVFW01000011.1 | JYXW01000003.1 | CTON01000002.1 | CTGK01000002.1 |
| LVFV01000011.1 | JYXT01000019.1 | CTOM01000004.1 | CTGJ01000035.1 |
| LVFT01000012.1 | JYXK01000009.1 | CTOL01000003.1 | CTGI01000004.1 |
| LVFS01000014.1 | JYXH01000002.1 | CTOK01000002.1 | CTGH01000004.1 |
| LVFR01000005.1 | JYXC01000008.1 | CTOJ01000001.1 | CTGG01000002.1 |
| LVFQ01000008.1 | JYWW01000034.1 | CTOI01000002.1 | CTGF01000002.1 |
| LVFP01000006.1 | JYWU01000014.1 | CTOH01000003.1 | CTGE01000002.1 |
| LVFO01000002.1 | JYWT01000009.1 | CTOG01000003.1 | CTGD01000002.1 |
| LVFN01000004.1 | JYWA01000003.1 | CTOF01000002.1 | CTGC01000002.1 |
| LVFM01000005.1 | JYVW01000007.1 | CTOE01000002.1 | CTGB01000004.1 |
| LVFL01000037.1 | JYVV01000004.1 | CTOD01000002.1 | CTGA01000002.1 |
| LVFK01000003.1 | JYVU01000035.1 | CTOC01000003.1 | CTFZ01000004.1 |
| LVFJ01000013.1 | JYVL01000001.1 | CTOB01000002.1 | CTFY01000002.1 |
| LVFI01000003.1 | JYVJ01000004.1 | CTOA01000004.1 | CTFX01000001.1 |
| LVFH01000010.1 | JYVG01000055.1 | CTNZ01000003.1 | CTFW01000003.1 |
| LUJG01000006.1 | JYVE01000037.1 | CTNY01000003.1 | CTFV01000004.1 |
| LUJF01000005.1 | JYUZ01000004.1 | CTNX01000002.1 | CTCJ01000002.1 |
| LUJE01000003.1 | JYUY01000010.1 | CTNW01000004.1 | CTCI01000003.1 |
| LUJC01000020.1 | JYUP01000020.1 | CTNV01000003.1 | CTGH01000003.1 |
| LUIZ01000005.1 | JYTX01000005.1 | CTNU01000002.1 | CTCG01000002.1 |
| LUIY01000005.1 | JYTW01000027.1 | CTNT01000002.1 | CTCF01000002.1 |
| LUIW01000007.1 | JYTU01000018.1 | CTNS01000003.2 | CTCE01000003.1 |
| LUIU01000061.1 | JYTT01000012.1 | CTNR01000001.1 | CTCD01000002.1 |
| UIT01000019.1 | JYTQ01000001.1 | CTNQ01000001.1 | CTCC01000044.1 |
| UIS01000029.1 | JYTP01000017.1 | CTNP01000002.1 | CTCB01000003.1 |
| LUIR01000027.1 | JYTL01000012.1 | CTNO01000002.1 | CTCA01000003.1 |
| LUIQ01000009.1 | JYTI01000010.1 | CTNN01000003.1 | CTBZ01000002.1 |
| LUIP01000019.1 | JYTD01000002.1 | CTNM01000002.1 | CTBY01000002.1 |
| LUIO001000023.1 | JYTB01000004.1 | CTNL01000002.1 | CTBX01000003.1 |
| LUIN01000035.1 | JYSY01000001.1 | CTNK01000004.1 | CTBW01000004.1 |

TABLE 2-continued

| Strains of *Salmonella Typhimurium* in which SEQ ID NO: 1 is 100% Conserved | | | |
|---|---|---|---|
| LUIM01000025.1 | JYSX01000031.1 | CTNJ01000001.1 | CTBV01000003.1 |
| LUIL01000040.1 | JYSO01000094.1 | CTNI01000002.1 | CTBU01000002.1 |
| LUIK01000041.1 | JYSN01000051.1 | CTNH01000002.1 | CTBT01000001.1 |
| LUIJ01000024.1 | JYSM01000007.1 | CTNG01000036.1 | CTBS01000003.1 |
| LUII01000036.1 | JYSL01000029.1 | CTNF01000003.1 | CTBR01000004.1 |
| LUIH01000014.1 | JYSG01000016.1 | CTNE01000002.1 | CTBQ01000003.1 |
| LUIG01000040.1 | JYSB01000024.1 | CTND01000002.1 | CTBP01000005.1 |
| LUIF01000036.1 | JYSA01000003.1 | CTNC01000001.1 | CTBO01000002.1 |
| LUIE01000017.1 | JYRX01000002.1 | CTNB01000046.1 | CTBN01000003.1 |
| LUID01000024.1 | JYRW01000014.1 | CTNA01000004.1 | CTBM01000003.1 |
| LUIC01000116.1 | JYRT01000085.1 | CTMZ01000002.1 | CTBK01000003.1 |
| LUIB01000040.1 | JYRQ01000034.1 | CTMY01000004.1 | CTBJ01000002.1 |
| LUIA01000027.1 | JYRM01000039.1 | CTMX01000002.1 | CTBI01000002.1 |
| LUHZ01000025.1 | JYRD01000017.1 | CTMW01000004.1 | CTBH01000003.1 |
| LUHY01000038.1 | JYRC01000016.1 | CTMV01000003.1 | CTBF01000004.1 |
| LUHX01000025.1 | JYQU01000020.1 | CTMU01000003.1 | CTBE01000004.1 |
| LUHV01000033.1 | JYQM01000015.1 | CTMT01000004.1 | CTBC01000002.1 |
| LUHU01000040.1 | JYQC01000008.1 | CTMS01000002.1 | CTBB01000002.1 |
| LUHT01000028.1 | JYQA01000030.1 | CTMR01000004.1 | CTBA01000002.1 |
| LUHS01000024.1 | JYPT01000005.1 | CTMQ01000003.1 | CTAZ01000003.1 |
| LUHR01000036.1 | JYPP01000050.1 | CTMP01000002.1 | CTAY01000001.1 |
| LONA01000003.1 | JYPO01000064.1 | CTMO01000003.1 | CTAX01000001.1 |
| LKJI01000024.1 | JYPM01000008.1 | CTMN01000003.1 | CTAW01000001.1 |
| LKJE01000032.1 | JUIT01000021.1 | CTMM01000003.1 | CTAV01000002.1 |
| LKJD01000006.1 | JRZW01000002.1 | CTML01000002.1 | CTAU01000001.1 |
| LJJK01000144.1 | JRZV01000001.1 | CTMK01000002.1 | CTAT01000003.1 |
| LIOJ01000001.1 | JRZU01000002.1 | CTMJ01000003.1 | CTAS01000002.1 |
| LIOG01000016.1 | JRZT01000030.1 | CTMI01000002.1 | CTAR01000002.1 |
| LIOF01000021.1 | JRZS01000015.1 | CTMH01000003.1 | CTAQ01000002.1 |
| LIOB01000013.1 | JRZR01000010.1 | CTMG01000002.1 | CTAP01000002.1 |
| LINM01000004.1 | JRZQ01000006.1 | CTMF01000002.1 | CTAO01000002.1 |
| LINL01000011.1 | JRZO01000062.1 | CTME01000001.1 | CTAN01000001.1 |
| LINK01000002.1 | JRZN01000054.1 | CTMD01000003.1 | CTAM01000004.1 |
| LINJ01000020.1 | JRZM01000003.1 | CTMC01000004.1 | CTAL01000003.1 |
| LINF01000009.1 | JRZL01000059.1 | CTMB01000002.1 | CTAK01000004.1 |
| LINE01000010.1 | JRZK01000010.1 | CTMA01000002.1 | CTAJ01000002.1 |
| LINB01000005.1 | SJRZJ01000012.1 | CTLZ01000002.1 | CTAI01000002.1 |
| LIMZ01000030.1 | SJRZI01000017.1 | CTLY01000002.1 | CTAH01000003.1 |
| LIMV01000008.1 | JRZH01000001.1 | CTLX01000004.1 | CTAG01000004.1 |
| LIMU01000022.1 | JRYU01000004.1 | CTLW01000002.1 | CTAF01000002.1 |
| LIMT01000027.1 | JRYT01000009.1 | CTLV01000004.1 | CTAE01000002.1 |
| LIMN01000012.1 | JRGW01000022.1 | CTLU01000001.1 | CTAD01000002.1 |
| LIMM01000010.1 | JRGV01000045.1 | CTLT01000004.1 | CTAC01000004.1 |
| LIMH01000001.1 | JRGU01000009.1 | CTLS01000004.1 | CTAB01000002.1 |
| LIDY01000003.1 | JRGT01000034.1 | CTLR01000003.1 | CQIE01000002.1 |
| LHOM01000023.1 | JRGS01000001.1 | CTLQ01000001.1 | CQHW01000002.1 |
| LHOJ01000006.1 | JRGR01000006.1 | CTLP01000003.1 | CQHV01000002.1 |
| LHOH01000004.1 | JHAI01000005.1 | CTLO01000001.1 | CQHU01000002.1 |
| LHOG01000003.1 | JHAH01000020.1 | CTLN01000003.1 | CQHS01000002.1 |
| LHOF01000033.1 | JHAG01000020.1 | CTLM01000004.1 | CQHR01000002.1 |
| LHNW01000001.1 | JHAF01000018.1 | CTLL01000004.1 | CQHQ01000002.1 |
| LHNS01000017.1 | JHAE01000013.1 | CTLK01000002.1 | CQHN01000002.1 |
| LHNM01000038.1 | FKJD01000009.1 | CTLJ01000002.1 | CQHJ01000001.1 |
| LHNL01000010.1 | FKJC01000004.1 | CTLI01000002.1 | CQHI01000002.1 |
| LHNI01000015.1 | FKJB01000003.1 | CTLH01000004.1 | CQHH01000002.1 |
| LHNH01000007.1 | CYID01000003.1 | CTLG01000004.1 | CQHG01000001.1 |
| LHNG01000002.1 | CYIC01000003.1 | CTLF01000002.1 | CQHF01000001.1 |
| LHMT01000026.1 | CYIB01000003.1 | CTLE01000002.1 | CQHE01000002.1 |
| LHMS01000025.1 | CYIA01000002.1 | CTLD01000004.1 | CQHD01000002.1 |
| LHMA01000007.1 | CYHZ01000003.1 | CTLC01000006.1 | CQHC01000002.1 |
| LHLX01000009.1 | CYHY01000003.1 | CTLB01000002.1 | CQHB01000002.1 |
| LHLU01000004.1 | CYHX01000003.1 | CTLA01000002.1 | CQHA01000001.1 |
| LHLP01000001.1 | CYHW01000002.1 | CTKZ01000002.1 | CQGZ01000001.1 |
| LHLO01000016.1 | CYHV01000002.1 | CTKI01000002.1 | CQGY01000002.1 |
| LHLK01000019.1 | CYHU01000003.1 | CTKG01000001.1 | CQGX01000002.1 |
| LHLF01000020.1 | CYHT01000003.1 | CTKD01000002.1 | CQGW01000002.1 |
| LHLA01000001.1 | CVMK01000002.1 | CTKC01000002.1 | CQGV01000002.1 |
| LHKL01000042.1 | CVMH01000002.1 | CTKB01000004.1 | CQGU01000002.1 |
| LHKK01000034.1 | CVKN01000003.1 | CTKA01000003.1 | CQGT01000001.1 |
| LHKD01000036.1 | CVKM01000005.1 | CTJZ01000002.1 | CQGS01000002.1 |
| LHKC01000003.1 | CVKK01000004.1 | CTJY01000002.1 | CQGR01000002.1 |
| LHKA01000038.1 | CVKJ01000005.1 | CTJX01000003.1 | CQGQ01000002.1 |
| LHJU01000003.1 | CVKH01000004.1 | CTJW01000002.1 | CQGP01000002.1 |
| LHJJ01000028.1 | CVKC01000002.1 | CTJV01000003.1 | CQGO01000002.1 |
| LHJF01000017.1 | CVKA01000004.1 | CTJU01000005.1 | CQGN01000002.1 |
| LHIX01000004.1 | CVJW01000001.1 | CTJT01000002.1 | CQGM01000002.1 |
| LHIW01000017.1 | CTQZ01000003.1 | CTJS01000002.1 | CQGL01000002.1 |
| LHIR01000013.1 | CTQY01000002.1 | CTJR01000003.1 | CQGK01000001.1 |

TABLE 2-continued

| Strains of *Salmonella Typhimurium* in which SEQ ID NO: 1 is 100% Conserved | | | |
|---|---|---|---|
| LHIQ01000047.1 | CTQX01000004.1 | CTJQ01000002.1 | CQGJ01000002.1 |
| LHIK01000014.1 | CTQU01000002.1 | CTJP01000002.1 | CQGI01000001.1 |
| LHIE01000015.1 | CTQT01000003.1 | CTJO01000004.2 | CQGH01000002.1 |
| LHID01000040.1 | CTQS01000002.1 | CTJN01000001.1 | CQGG01000002.1 |
| LHHK01000011.1 | CTQR01000002.1 | CTJM01000004.1 | CIJW01000002.1 |
| LHHB01000001.1 | CTQQ01000001.1 | CTJK01000003.1 | CIJD01000002.1 |
| LHGZ01000002.1 | CTQP01000002.1 | CTJJ01000002.1 | CHJY01000001.1 |
| LHGY01000001.1 | CTQO01000002.1 | CTIL01000002.1 | CGGH01000001.1 |
| LHGL01000047.1 | CTQN01000002.1 | CTIK01000003.1 | CGDA01000002.1 |
| LHGJ01000005.1 | CTQM01000002.1 | CTIJ01000003.1 | CGCS01000001.1 |
| LHGI01000006.1 | CTQL01000098.1 | CTII01000002.1 | CGCQ01000002.1 |
| LHGH01000003.1 | CTQK01000004.1 | CTIH01000002.1 | CGCH01000002.1 |
| LHFW01000031.1 | CTQJ01000002.1 | CTIG01000002.1 | CFOA01000002.1 |
| LHFV01000044.1 | CTQI01000001.1 | CTIF01000004.1 | CFNX01000002.1 |
| LHFU01000031.1 | CTQH01000001.1 | CTIE01000003.1 | CFLD01000002.1 |
| LHFT01000032.1 | CTQG01000002.1 | CTID01000002.1 | BAKU01000002.1 |
| LHFS01000022.1 | CTQF01000003.1 | CTIC01000002.1 | AYVJ01000114.1 |
| LHFP01000043.1 | CTQE01000004.1 | CTIB01000003.1 | AYUQ01000108.1 |
| LHFF01000013.1 | CTQD01000002.1 | CTIA01000004.1 | AUXR01000008.1 |
| LHEY01000021.1 | CTQC01000001.1 | CTHZ01000002.1 | AUXE01000003.1 |
| EHEX01000008.1 | CTQB01000003.1 | CTHY01000001.1 | AUVE01000003.1 |
| LHEW01000017.1 | CTQA01000002.1 | CTHX01000001.1 | AUVD01000043.1 |
| LHEV01000005.1 | CTPZ01000003.1 | CTHW01000001.1 | AUQU01000045.1 |
| LHER01000004.1 | CTPY01000003.1 | CTHV01000002.1 | AUQT01000034.1 |
| LHEQ01000025.1 | CTPX01000004.1 | CTHU01000002.1 | AUQO01000062.1 |
| LHEP01000049.1 | CTPW01000002.1 | CTHT01000004.1 | AUQN01000039.1 |
| LHEA01000005.1 | CTPV01000002.1 | CTHS01000002.1 | AUQM01000038.1 |
| LFGM01000013.1 | CTPU01000005.1 | CTHR01000002.1 | AOXO01000096.1 |
| LFDY01000028.1 | CTPT01000001.1 | CTHQ01000002.1 | AOXD01000065.1 |
| LFDW01000010.1 | CTPS01000002.1 | CTHP01000002.1 | AOXC01000083.1 |
| LFCC01000059.1 | CTPR01000003.1 | CTHO01000004.1 | AJTU01000007.1 |
| LDPA01000008.1 | CTPQ01000002.1 | CTHN01000002.1 | AHVA01000018.1 |
| LAPQ01000066.1 | CTPP01000002.1 | CTHM01000002.1 | AHUZ01000018.1 |
| LAPP01000078.1 | CTPO01000002.1 | CTHL01000002.1 | AHUV01000085.1 |
| LAPO01000058.1 | CTPN01000002.1 | CTHK01000002.1 | AHUT01000031.1 |
| LAPN01000091.1 | CTPM01000005.1 | CTHJ01000001.1 | AHUS01000047.1 |
| LAPM01000076.1 | CTPL01000004.1 | CTHI01000039.1 | AERV01000023.1 |
| LAPH01000042.1 | CTPK01000003.1 | CTHH01000002.1 | ABAO01000006.1 |
| LAPG01000091.1 | CTPJ01000002.1 | CTHG01000002.1 | LUIV01000062.1 |

Also based on a publicly available software (e.g., BLAST), SEQ ID NO:1 is partially conserved (e.g., at least 99% sequence identity) in 48 *Salmonella typhimurium* strains listed by Genbank accession number in Table 3.

TABLE 3

| Strains of *Salmonella Typhimurium* in which SEQ ID NO: 1 is Partially Conserved | | | |
|---|---|---|---|
| LVGO01000006.1 | LUJA01000002.1 | LDYH01000006.1 | AMEA02000013.1 |
| LVGE01000003.1 | LUIX01000003.1 | JYPX01000009.1 | AMDZ02000027.1 |
| LVGD01000004.1 | LFGR01000011.1 | JTED01000004.1 | AMDY01000216.1 |
| LVGC01000003.1 | LFGQ01000013.1 | AUQV01000023.1 | AMDX02000108.1 |
| LVGB01000001.1 | LFGP01000017.1 | ATWR01000084.1 | JRZX01000002.1 |
| LVGA01000003.1 | LFGN01000015.1 | AMEH02000182.1 | JRZP01000003.1 |
| LVFZ01000005.1 | LFDX01000009.1 | AMEG02000055.1 | AUQL01000040.1 |
| LVFY01000001.1 | LFCI01000010.1 | AMEF02000044.1 | LFGO01000009.1 |
| LVFX01000003.1 | LFCH01000028.1 | AMEE02000031.1 | LFDZ01000012.1 |
| LVFU01000005.1 | LFCG01000008.1 | AMED02000059.1 | LECA01000009.1 |
| LUJD01000002.1 | LECD01000013.1 | AMEC02000055.1 | LUHW01000058.1 |
| LUJB01000005.1 | LECC01000010.1 | AMEB02000105.1 | LECB01000012.1 |

Based on a publicly available software (e.g., BLAST), SEQ ID NO:1 is not found in the following non-*Typhimurium salmonella* strains:

*Salmonella_enterica*_serovar_Ohio_CFSAN001079
*Salmonella_enterica*_serovar_Newport_WA14881
*Salmonella_enterica*_serovar_Schwarzengrund_SL480
*Salmonella_enterica*_serovar_*Gallinarum*_28791
*Salmonella_enterica*_serovar_Thompson_2010K1863
*Salmonella_enterica*_serovar_Kentucky_CDC191
*Salmonella_enterica*_serovar_*Typhi*_BL196
*Salmonella_enterica*_serovar_*Enteritidis*_P125109
*Salmonella_enterica*_serovar_Agona_72A52
*Salmonella_enterica*_serovar_Saintpaul_JO2008
*Salmonella_enterica*_serovar_Heidelberg_SL476
*Salmonella_enterica*_serovar_Virchow_ATCC51955
*Salmonella_enterica*_serovar_Paratyphi_B_SARA62
*Salmonella_enterica*_serovar_MontevideoMDA09249507
*Salmonella_enterica*_serovar_Muenchen_2009K0951

*Salmonella_enterica*_serovar_B areilly_CFSAN000197
*Salmonella_enterica*_serovar_Virchow_SL491
*Salmonella_enterica*_serovar_Pullorum_19945
*Salmonella_enterica*_serovar_Dublin_SL1438
*Salmonella_enterica*_serovar_Stanley_060538

In another embodiment, a detection method is based on the identification of residues 749-1697 of *Salmonella typhimurium* ACCESSION CP007235 REGION: 658819 . . . 662133 (see SEQ ID NO:2 in Table 1). In another embodiment, a detection method is based on the identification of residues 755-1063 of *Salmonella typhimurium* ACCESSION CP007235 REGION: 658819 . . . 662133 (see SEQ ID NO:3 in Table 1). In some embodiments, the detection method incorporates unlabeled primers and labeled probes for the detection of *Salmonella typhimurium*.

Oligonucleotides

Oligonucleotides of the instant invention are set forth in SEQ ID NOs: 4-9.

Disclosed oligonucleotides can be used as primers for PCR amplification and as hybridization probes. Primers and probes are shown in Table 1.

The nucleic acid probes can contain a detectable label. In some embodiments, the probe comprises a reporter-quencher combination as employed in a double-stranded probe, a TAQMAN™ probe, a molecular beacon probe, a SCORPION™ probe, a dual hybridization probe, or an ECLIPSE™ probe. In some embodiments, a double-stranded probe comprises two completely or partially complementary strands. In some embodiments, one strand of the double-stranded probe comprises a reporter on the 5' end and the other strand comprises a quencher on the 3' end such that when the two strands hybridize, the reporter and quencher face each other and the quencher quenches the fluorescence emitted by the reporter. During PCR, the strands separate, allowing the reporter to fluoresce and to be detected. In some embodiments, each strand of the double-stranded probe includes a reporter at one end (e.g., the 5' end) and a quencher at the other end (e.g., the 3' end). When the two strands hybridize with each other, the reporter from the first strand is in close proximity with the quencher of the second strand such that fluorescence quenching occurs. During PCR, the strands separate, allowing the reporter to fluoresce and to be detected. In an embodiment, the probe is a double-stranded probe as described in U.S. Pat. No. 9,194,007, which is incorporated by reference in its entirety herein. In an embodiment, a reporter-quencher pair used in a double-stranded probe is 6-FAM and Iowa Black® FQ.

III. METHODS

The oligonucleotides can be used in a method for selectively detecting the presence of *Salmonella typhimurium* in a sample. In an embodiment, the method begins by providing a reaction mixture comprising a suitable primer pair for amplification of residues 749-1697, or a portion thereof, of SEQ ID NO:2. In some embodiments, the reaction mixture comprises a primer pair for amplification of a sequence 95%, 97%, or 99% homologous to SEQ ID NO:2. In some embodiments, the reaction mixture comprises a primer pair for amplification of a sequence of SEQ ID NO:2 or a portion thereof.

In certain embodiments, the reaction mixture comprises a primer pair for amplification of residues 755-1063, or portions thereof, of SEQ ID NO:3. In some embodiments, the reaction mixture comprises a primer pair for amplification of a sequence 95%, 97%, or 99% homologous to SEQ ID NO:3. In some embodiments, the reaction mixture comprises a primer pair for amplification of a sequence of SEQ ID NO:3 or a portion thereof. In some embodiments, the primer pair for amplification of the nucleic acid region of SEQ ID NO:3 comprises SEQ ID NO:4 and SEQ ID NO:5.

In some embodiments, the method further comprises a probe for the nucleic acid region to be detected. In certain embodiments, the probe comprises a detectable label. In some embodiments, the probe is a single-stranded probe comprising SEQ ID NO:6, SEQ ID NO:7, SEQ ID NO:8, or SEQ ID NO:9. In some embodiments, each probe is labeled with a reporter on one end (e.g., the 5' end) and a quencher on the other end (e.g., the 3' end). In some embodiments, the probe is a double-stranded probe comprising SEQ ID NO:6 and SEQ ID NO:7 (e.g., SEQ ID NO:6 can hybridize to SEQ ID NO:7) with each strand having a reporter on one end (e.g., the 5' end) and a quencher on the other end (e.g., the 3' end).

The next step of the method comprises performing PCR amplification (e.g., real-time PCR) of the nucleic acids of the sample using the reaction mixture. In some embodiments, PCR amplification is performed in partitions (e.g, droplets). Methods and compositions for partitioning a solution are described, for example, in published patent applications WO 2012/135259, WO 2014/117088, WO 2010/036352, and U.S. Pat. No. 9,156,010, the entire content of each of which is incorporated by reference herein.

In the last step of the method, the presence of *Salmonella typhimurium* is selectively detected by detecting the amplified nucleic acids. In some embodiments, the detecting step comprises sequencing the amplified nucleic acids.

IV. KITS

In another aspect, kits for detecting *Salmonella typhimurium* in a sample according to the methods described herein are provided. In some embodiments, a kit comprises a primer pair as described herein. In some embodiments, the kit further comprises probes as described herein. In some embodiments, the kit further comprises assay components including, but not limited to, a lysis reagent, a DNA polymerase, dNTPs, a buffer, a negative control, and a positive control. In some embodiments, the kit further comprises instructions for carrying out the methods described herein.

V. EXAMPLES

Example 1—Comparison of *Salmonella typhimurium* Assay of the Instant Invention to *Salmonella* Spp. Assay In this example, the *Salmonella typhimurium* assay of the instant invention was compared to a commercially available *Salmonella* spp. Assay. In the experiment, eleven *Salmonella* serovars that are most relevant for the food industry were tested with the *Salmonella typhimurium* assay of this disclosure and with the iQ-Check *Salmonella* spp. II Assay (Bio-Rad). The eleven *Salmonella* strains were streaked on a TCS Petri dish and allowed to grow for 24 hr at 37° C. Individual colonies were then picked, diluted in 500 µL sterile water and 5 µL were tested with each assay using the Bio-Rad CFX96 Touch™ Real-Time PCR Detection System. For the *Salmonella typhimurium* assay, the double-stranded probe comprised SEQ ID NOs 6 and 7. Each strand of the double-stranded probe was labeled with 6-FAM on the 5' end and Iowa Black™ FQ on the 3'end. The double-stranded probe was synthesized by Integrated DNA Technologies using phosphoramidite chemistry. Results are shown in Table 4.

TABLE 4

Comparison of Assays

| | Bio-Rad iQ-Check *Salmonella* spp. II assay | | | *Salmonella Typhimurium* assay | | |
|---|---|---|---|---|---|---|
| Serovars | Target Cq | Internal control Cq | Result | Target Cq | Internal control Cq | Result |
| Negative Ctrl | N/A | 32.84 | Negative | N/A | 32.49 | Negative |
| Positive Ctrl | 31.72 | 32.24 | Positive | 31.95 | 31.78 | Positive |
| *Typhimurium* | 19.69 | 34.60 | Positive | 19.36 | 33.43 | Positive |
| Monophasic *Typhimurium* | 18.35 | N/A | Positive | 18.08 | 34.2 | Positive |
| Enteritidis | 20.34 | 32.72 | Positive | N/A | 32.15 | Negative |
| Infantis | 20.86 | 32.40 | Positive | N/A | 31.78 | Negative |
| Virchow | 19.71 | 33.28 | Positive | N/A | 32 | Negative |
| Hadar | 21,20 | 32.29 | Positive | N/A | 31.89 | Negative |
| Paratyphi B Java | 20.24 | 33.27 | Positive | N/A | 31.91 | Negative |
| Livingstone | 20.84 | 33.21 | Positive | N/A | 32.38 | Negative |
| Kentucky | 18.67 | 34.26 | Positive | N/A | 32.17 | Negative |
| Dublin | 21,24 | 32.68 | Positive | N/A | 31.99 | Negative |
| Newport | 20.23 | 32.67 | Positive | N/A | 31.98 | Negative |

The results shown in Table 4 illustrate that only *typhimurium* is detected by the *Salmonella Typhimurium* assay. The results also show that the sensitivities of both assays are identical and that the *Salmonella typhimurium* assay can be used as a primary screening assay or as a confirmatory, serotyping assay.

Example 2—Assay Selectivity

This example illustrates assay selectivity of the instant invention. One-hundred and nine *Salmonella enterica* subsp. *enterica* serovars and *Salmonella enterica* subspecies (in italics in Table 4) were tested with the *Salmonella typhimurium* assay. The same method and probes as in Example 1 were used in this experiment. The organisms tested are shown in Table 5.

TABLE 5

| Selectivity |
|---|
| Abaetetuba |
| Aberdeen |
| Adelaïde |
| Agama |
| Albany |
| Anatum |
| *arizonae** |
| Bambylor |
| Bareilly |
| Berta |
| Betioky |
| Blegdam |
| Blockley |
| *bongori* |
| Braenderup |
| Brandenburg |
| Bredeney |
| Budapest |
| California |
| Cerro |
| Carrau |
| Canoga |
| Crossness |
| Cubana |
| *Choleraesuis* |
| *diarizonae** |
| Dalhem |
| Derby |
| Dublin |
| Emek |
| Duisberg |

TABLE 5-continued

| Selectivity |
|---|
| Enteritidis |
| Fischerkietz |
| Ferruch |
| Give |
| Gaminara |
| Gallinarum |
| Glostrup |
| Grumpensis |
| Grabow |
| Goldgoast |
| Havana |
| Hadar |
| Guinea |
| Havanna |
| *houtenae** |
| Illinois |
| Heidelberg |
| Indiana |
| *indica** |
| Inverness |
| Johannesburg |
| Infantis |
| Kentucky |
| Kirkee |
| Kottbus |
| Kedougou |
| Lomita |
| Livingstone |
| Manica |
| London |
| Miami |
| Minnesota |
| Maregrosso |
| Mbandaka |
| Muenchen |
| Montevideo |
| Moscow |
| Napoli |
| Nienstedten |
| Naestved |
| Newport |
| Nottingham |
| Oranienburg |
| Ouakam |
| Okatie |
| Ohio |
| Phoenix |
| Panama |
| Paratyphi B** |
| Paratyphi B java |
| Postdam |
| Poona |

TABLE 5-continued

Selectivity

Puttin
Quentin
Rostock
Salamae
Rubislaw
Senftenberg
Saint Paul
Schwarzengrund
Singapore
Sheffield
Sundsvall
Springs
Strasbourg
Taksony
Tallahassee
Tournai
Tenessee
Thompson
Treforest
Tranoroa
Utrecht
Virchow
Zuerich
Yoruba
Wayne
Worthington Of the organisms listed in Table 5, all but Paratyphi B were not detected with the assay. The results illustrate that the *Salmonella typhimurium* assay is highly selective for *Salmonella typhimurium*.

Example 3—Assay Exclusivity

This example illustrates assay exclusivity of the instant invention. Thirty-nine non-*Salmonella* bacteria were tested with the *Salmonella typhimurium* assay. The same method and probe as in Example 1 was used in this experiment. The bacteria tested are tabulated in Table 6. None of the bacteria listed in Table 6 were detected by the *Salmonella typhimurium* assay, illustrating assay exclusivity.

TABLE 6

Exclusivity

*Acinetobacter baumanii*
*Aeromonas hydrophila*
*Aeromonas hydrophila/caviae*
*Bacillus licheniformis*
*Bacillus cereus*
*Campylobacter jejuni*
*Campylobacter coli*
*Campylobacter lari*
*Campylobacter upsaliensis*
*Citrobacter freundii*
*Cronobacter sakazakii*
*Enterobacter cloacae*
*Enterobacter pyrinus*
*Enterobacter sakazakii*
*Enterobacter aerogenes*
*Enterobacter asburiae*
*Enterobacter amnigenus*
*Enterobacter cowanii*
*Enterococcus faecium*
*Escherichia coli*
*Escherichia hermanii*
*Hafnia alvei*
*Klebsiella oxytoca*
*Klebsiella pneumoniae*
*Listeria monocytogenes*
*Micrococcus luteus*
*Pantoea agglomerans*
*Proteus mirabilis*
*Pseudomonas fluorescens*
*Pseudomonas aeruginosa*
*Raoultella terrigena*
*Serratia marcescens*
*Shigella flexneri*
*Shigella sonnei*
*Staphylococcus aureus*
*Staphylococcus internmedius*
*Staphylococcus xylosus*
*Staphylococcus epidermidis*
*Yersinia enterocoloitica*

Example 4—Assay Specificity

This example illustrates assay specificity of the instant invention. Seventy-nine *Salmonella typhimurium* serovars were tested with the *Salmonella typhimurium* assay. The same method and probe as in Example 1 was used in this experiment. The bacteria tested are tabulated in Table 7. All of the bacteria listed in Table 7 were detected by the *Salmonella typhimurium* assay, illustrating assay specificity.

TABLE 7

Specificity

| Serovar | Antigenic formula | Comment | Primary source | Origin | Strain number (Bio-Rad Library) | Strain number (Other Library) |
|---|---|---|---|---|---|---|
| Typhimurium | 1,4,[5],12:i:1,2 | | Anses | Brine | 002 | no Anses: 38.09 |
| Typhimurium | 1,4,[5],12:i:1,2 | | Anses | Beef meat | 003 | no Anses: 442.09 |
| Typhimurium | 1,4,[5],12:i:1,2 | | Anses | Pork (crépine de porc) | 004 | no Anses: 447.09 |
| Typhimurium | 1,4,[5],12:i:1,2 | | Anses | Lamb with sauce | 005 | no Anses: 591.09 |
| Typhimurium | 1,4,[5],12:i:1,2 | | Anses | Stuffed quail | 006 | no Anses: 695.09 |
| Typhimurium | 1,4,[5],12:i:1,2 | | Anses | Culture from lamb feces | 007 | no Anses: 839.09 |
| Typhimurium | 1,4,[5],12:i:1,2 | | Anses | Environment (Duck) | 008 | no Anses: 838.09 |
| Typhimurium | 1,4,[5],12:i:1,2 | | Anses | Culture from horse feces | 009 | no Anses: 553.11 |
| Typhimurium | 1,4,[5],12:i:1,2 | | Anses | White pepper | 010 | no Anses: 564.11 |
| Typhimurium | 1,4,[5],12:i:1,2 | | Anses | Hoki filet with cream | 011 | no Anses: 708.11 |

TABLE 7-continued

| Serovar | Antigenic formula | Comment | Primary source | Origin | Strain number (Bio-Rad Library) | Strain number (Other Library) |
|---|---|---|---|---|---|---|
| Typhimurium | 1,4,[5],12:i:1,2 | | Anses | Pigeon viscera | 012 | no Anses: 781.11 |
| Typhimurium | 1,4,[5],12:i:1,2 | | Anses | Compost | 013 | no Anses: 792.11 |
| Typhimurium | 1,4,[5],12:i:1,2 | | Anses | Environmental (Chicken) | 014 | no Anses: 835.11 |
| Typhimurium | 1,4,[5],12:i:1,2 | | Anses | Streaky ham | 015 | no Anses: 840.11 |
| Typhimurium | 1,4,[5],12:i:1,2 | | Anses | Whole quail | 016 | no Anses: 845.11 |
| Typhimurium | 1,4,[5],12:i:1,2 | | Anses | Spareribs | 017 | no Anses: 880.11 |
| Typhimurium | 1,4,[5],12:i:1,2 | | Anses | Culture from swine feces | 018 | no Anses: 886.11 |
| Typhimurium | 1,4,[5],12:i:1,2 | | Anses | Raw milk (cow) | 019 | no Anses: 907.11 |
| Typhimurium | 1,4,[5],12:i:1,2 | | Anses | Sausage | 020 | no Anses: 976.11 |
| Typhimurium | 1,4,[5],12:i:1,2 | | Anses | Tomato filling | 021 | no Anses: 977.11 |
| Typhimurium | 1,4,[5],12:i:1,2 | | Anses | Stuffed potatoes | 022 | no Anses: 979.11 |
| Typhimurium | 1,4,[5],12:i:1,2 | | Anses | Fish meal | 023 | no Anses: 985.11 |
| Typhimurium | 1,4,[5],12:i:1,2 | | Anses | Pet food | 043 | no Anses: 1175.11 |
| Typhimurium | 1,4,[5],12:i:1,2 | | Anses | Foie gras (Liver) | 030 | no Anses: 119.11 |
| Typhimurium | 1,4,[5],12:i:1,2 | | ADRIA Development | Milk powder | 081 | ADRIA no4 |
| Typhimurium | 1,4,[5],12:i:1,2 | | ADRIA Development | Pasteurized liquid egg | 082 | ADRIA no13 |
| Typhimurium | 1,4,[5],12:i:1,2 | | ADRIA Development | Pasteurized liquid egg | 083 | ADRIA no206 |
| Typhimurium | 1,4,[5],12:i:1,2 | | ADRIA Development | Egg yolk | 084 | ADRIA no472 |
| Typhimurium | 1,4,[5],12:i:1,2 | | ADRIA Development | Pasteurized liquid egg | 085 | ADRIA no776 |
| Typhimurium | 1,4,[5],12:i:1,2 | | ADRIA Development | Ready-to-eat | 086 | CIP 58.58 |
| Typhimurium | 1,4,[5],12:i:1,2 | | ADRIA Development | Foie (Liver) | 087 | ADRIA no19 |
| Typhimurium | 1,4,[5],12:i:1,2 | | ADRIA Development | Raw ground meat | 088 | ADRIA no22 |
| Typhimurium | 1,4,[5],12:i:1,2 | | ADRIA Development | Ready-to-eat | 089 | ADRIA no167 |
| Typhimurium | 1,4,[5],12:i:1,2 | | ADRIA Development | Chipolatas sausages | 090 | ADRIA no193 |
| Typhimurium | 1,4,[5],12:i:1,2 | | ADRIA Development | Chipolatas sausages | 091 | ADRIA no830 |
| Typhimurium | 1,4,[5],12:i:1,2 | | ADRIA Development | Merguez sausages | 092 | ADRIA no911 |
| Typhimurium | 1,4,[5],12:i:1,2 | | ADRIA Development | Chipolatas sausages | 093 | ADRIA no987 |
| Typhimurium | 1,4,[5],12:i:1,2 | | ADRIA Development | Meat (pâté) | 094 | ADRIA no4874 |
| Typhimurium | 1,4,[5],12:i:1,2 | | ADRIA Development | Frozen meat | 095 | A00C003 |
| Typhimurium | 1,4,[5],12:i:1,2 | | ADRIA Development | Frozen meat | 096 | A00C004 |
| Typhimurium | 1,4,[5],12:i:1,2 | | ADRIA Development | Frozen beef trim | 097 | A00C059 |
| Typhimurium | 1,4,[5],12:i:1,2 | | ADRIA Development | ground beef | 098 | A00C060 |
| Typhimurium | 1,4,[5],12:i:1,2 | | ADRIA Development | Pork | 106 | Ad1070 |
| Typhimurium | 1,4,[5],12:i:1,2 | | ADRIA Development | Pork | 107 | ST325 |
| Typhimurium | 1,4,[5],12:i:1,2 | | ADRIA Development | Pork | 108 | ST1 |
| Typhimurium | 1,4,[5],12:i:1,2 | | ADRIA Development | Pork | 109 | ST394 |
| Typhimurium | 1,4,[5],12:i:1,2 | | ADRIA Development | Pork | 110 | ST719 |
| Typhimurium | 1,4,[5],12:i:1,2 | | ADRIA Development | Pork | 111 | ST11 |
| Typhimurium | 1,4,[5],12:i:1,2 | | ADRIA Development | Liquid egg | 113 | JES411 |

TABLE 7-continued

| Serovar | Antigenic formula | Comment | Primary source | Origin | Strain number (Bio-Rad Library) | Strain number (Other Library) |
|---|---|---|---|---|---|---|
| *Typhimurium* | 1,4,[5],12:i:1,2 | | ADRIA Development | Beef trim | 116 | Ad913 |
| *Typhimurium* | 1,4,[5],12:i:1,2 | | ADRIA Development | Pork | 118 | Ad1249 |
| *Typhimurium* | 1,4,[5],12:i:1,2 | | ADRIA Development | pork (crépine) | 119 | Ad1338 |
| *Typhimurium* | 1,4,[5],12:i:1,2 | | ADRIA Development | ground meat | 120 | Ad1410 |
| *Typhimurium* | 1,4,[5],12:i:1,2 | | ADRIA Development | Liquid egg | 121 | Ad1484 |
| *Typhimurium* | 1,4,[5],12:i:1,2 | | ADRIA Development | Drinking water from trough | 122 | Ad1546 |
| *Typhimurium* | 1,4,[5],12:i:1,2 | | ADRIA Development | salmon with vegetables | 123 | Ad1603 |
| *Typhimurium* | 1,4,[5],12:—:— | non motile variant | ADRIA Development | Tiramisu | 124 | Ad1333 |
| *Typhimurium* | 1,4,[5],12:—:1,2 | monophasic variant | ADRIA Development | Hen | 125 | Ad1335 |
| *Typhimurium* | 1,4,[5],12:i:— | monophasic variant | ADRIA Development | Pork specialty | 126 | Ad1334 |
| *Typhimurium* | 1,4,[5],12:i:1,2 | | Anses | Environmental (Quail) | 160 | 2002LSAL00347 |
| *Typhimurium* | 1,4,[5],12:i:1,2 | | Anses | Environmental (goose) | 161 | 2016LSAL02607 |
| *Typhimurium* | 1,4,[5],12:i:— | monophasic variant | Anses | Environmental (Pork) | 162 | 2009LSAL04410 |
| *Typhimurium* | 1,4,[5],12:—:1,2 | monophasic variant | Anses | Environmental (*Gallus gallus*-hen) | 163 | 2010LSAL01759 |
| *Typhimurium* | 1,4,[5],12:i:— | monophasic variant | Anses | Environmental | 164 | 2011LSAL04681 |
| *Typhimurium* | 1,4,[5],12:i:— | monophasic variant | Anses | Environmental (Turkey) | 165 | 2012LSAL04635 |
| *Typhimurium* | 1,4,[5],12:i:1,2 | | Anses | Environmental (*Gallus gallus*) | 166 | 2013LSAL00987 |
| *Typhimurium* | 1,4,[5],12:i:— | monophasic variant | Anses | Environmental (Bovine) | 167 | 2014LSAL00857 |
| *Typhimurium* | 1,4,[5],12:i:— | monophasic variant | Anses | Pork meat | 168 | 2011LSAL06561 |
| *Typhimurium* | 1,4,[5],12:i:— | monophasic variant | Anses | Veal meat | 169 | 2012LSAL05317 |
| *Typhimurium* | 1,4,[5],12:i:— | monophasic variant | Anses | Turkey meat | 170 | 2014LSAL02635 |
| *Typhimurium* | 1,4,[5],12:i:— | monophasic variant | Anses | *Gallus gallus* meat | 171 | 2014LSAL03913 |
| *Typhimurium* | 1,4,[5],12:i:— | monophasic variant | Anses | Poultry Feed | 172 | 2011LSAL04983 |
| *Typhimurium* | 1,4,[5],12:i:— | monophasic variant | Anses | cattle feed | 173 | 2012LSAL03407 |
| *Typhimurium* | 1,4,[5],12:i:— | monophasic variant | Anses | animal blood products | 174 | 2012LSAL03874 |
| *Typhimurium* | 1,4,[5],12:i:— | monophasic variant | Anses | cattle feed | 175 | 2015LSAL00792 |
| *Typhimurium* | 1,4,[5],12:i:— | monophasic variant | Anses | beef meat (carcass) | 176 | 2013LSAL02030 |
| *Typhimurium* | 1,4,[5],12:i:— | monophasic variant | Anses | pork (carcass) | 177 | 2015LSAL01461 |
| *Typhimurium* | 1,4,[5],12:i:— | monophasic variant | Anses | turkey (carcass) | 178 | 2013LSAL03886 |
| *Typhimurium* | 1,4,[5],12:i:— | monophasic variant | Anses | chicken (carcass) | 179 | 2016LSAL00194 |

It is understood that the examples and embodiments described herein are for illustrative purposes only and that various modifications or changes in light thereof will be suggested to persons skilled in the art and are to be included within the spirit and purview of this application and scope of the appended claims. All patents, patent applications, internet sources, and other published reference materials cited in this specification are incorporated herein by reference in their entireties. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

The invention claimed is:

1. A method of selectively detecting the presence of *Salmonella typhimurium* in a sample comprising nucleic acids, the method comprising:
   (a) providing a reaction mixture comprising (i) a suitable primer pair for amplification of an amplicon polynucleotide, which amplicon polynucleotide consists of a nucleic acid at least 95% homologous to SEQ ID NO:3 and (ii) the nucleic acids of the sample;
   (b) performing PCR amplification of the nucleic acids of the sample using the reaction mixture of step (a) to form the amplicon polynucleotide primed by the primer pair; and
   (c) selectively detecting the presence of *Salmonella typhimurium* by detecting the amplicon polynucleotide.

2. The method of claim 1, wherein the reaction mixture comprises a primer pair for amplification of an amplicon polynucleotide at least 97% homologous to SEQ ID NO:3.

3. The method of claim 1, wherein the reaction mixture comprises a primer pair for amplification of a polynucleotide at least 99% homologous to SEQ ID NO:3.

4. The method of claim 1, wherein the reaction mixture comprises a primer pair for amplification of an amplicon polynucleotide consisting of SEQ ID NO:3.

5. The method of claim 1, wherein the primer pair comprises SEQ ID NO:4 and SEQ ID NO:5.

6. The method of claim 5, wherein the reaction mixture further comprises a probe for the amplicon polynucleotide.

7. The method of claim 6, wherein the probe comprises a detectable label.

8. The method of claim 6, wherein the probe comprises SEQ ID NO:6, SEQ ID NO:7, SEQ ID NO:8, or SEQ ID NO:9.

9. The method of claim 6, wherein the probe is selected from the group consisting of a double-stranded probe, a molecular beacon probe, and a dual hybridization probe.

10. The method of claim 1, wherein the detecting the presence of *Salmonella typhimurium* comprises sequencing the amplicon polynucleotide.

11. The method of claim 1, wherein step (b) is performed in partitions.

* * * * *